United States Patent [19]

Heidmann et al.

[11] Patent Number: 5,583,022

[45] Date of Patent: Dec. 10, 1996

[54] DEFECTIVE RECOMBINANT RETROVIRUS

[75] Inventors: Thierry Heidmann, Paris; Jean-François Nicolas, Noisy, both of France

[73] Assignees: Institut Pasteur; Institut National de la Sante et de la Recherche Medicale, both of Paris Cedex, France

[21] Appl. No.: 298,181

[22] Filed: Aug. 30, 1994

Related U.S. Application Data

[63] Continuation of Ser. No. 3,680, Jan. 13, 1993, abandoned, which is a continuation of Ser. No. 331,351, Mar. 31, 1989, abandoned.

[30] Foreign Application Priority Data

Mar. 31, 1988 [FR] France .................... 88 04332

[51] Int. Cl.⁶ ............... C12N 15/86; C12N 5/10; C12N 15/00; C12N 15/63
[52] U.S. Cl. ................... 435/172.3; 435/320.1
[58] Field of Search ............... 435/320.1, 172.3

[56] References Cited

FOREIGN PATENT DOCUMENTS

| | | |
|---|---|---|
| 0162319 | 11/1985 | European Pat. Off. |
| 0178220 | 4/1986 | European Pat. Off. |
| 0237157 | 9/1987 | European Pat. Off. |
| WO86/00922 | 2/1986 | WIPO |

OTHER PUBLICATIONS

McCormick, *Biotechnology*, vol. 3, No. 8, pp. 689–693 (1985).

Yakult Honsha Co. Ltd., *Patent Abstracts of Japan*, vol. 11, No. 246 (C-439) (1987).

Anderson et al. Chemical Abstracts, vol. 99, No. 1, pp. 163–164, 17374s (1983).

S.-F. Yu et al. (1986) Proc. Natl. Acad. Sci. USA 83:3194–3198.

M.-C. Magli et al. (1987) Proc. Natl. Acad. Sci USA 84:789–793.

D. Armentano et al. (1987) J. Virol. 61:1647–1650.

K. Shimotohno et al. (1981) Cell 26:67–71.

J. R. McLachlin et al (1990) Prog. in Nucl. Acid Res. and Mol. Biol. 38:91–135.

T. Heidmann et al (1988) Proc. Natl. Acad Sci. USA 85:2219–2223.

*Primary Examiner*—Mindy Fleisher
*Assistant Examiner*—Johnny F. Railey, II
*Attorney, Agent, or Firm*—Oblon, Spivak, McClelland, Maier, & Neustadt, P.C.

[57] ABSTRACT

The invention relates to a defective recombinant retrovirus containing a sequence coding for a specific protein in the genome of the cells. The DNA of the recombinant retrovirus contains the sequence coding for the protein intercalated between an acceptor splicing site and a donor splicing site, the whole assembly being placed under the control of a suitable promoter under conditions such that the infection of the said cells by this recombinant retrovirus is accompanied by the incorporation of the sequence coding for the protein into the genome of the infected cells.

12 Claims, 6 Drawing Sheets

DEFECTIVE RECOMBINANT RETROVIRUS

This application is a continuation of application Ser. No. 08/003,680, filed on Jan. 13, 1993, now abandoned, which is a continuation of application Ser. No. 07/331,351, filed Mar. 31, 1989, now abandoned.

The present invention relates to "agents" for use in the integration of sequences coding for specific proteins in the genome of cells of eucaryotic cell lines, in particular those of mammals. More particularly, the present invention relates to cell lines capable of being infected by a wild type retrovirus. Still more particularly, the present invention relates to the integration of such coding sequences under conditions such that they can be expressed within these infected cells.

In its final form, the "agent" according to the present invention consists of a defective recombinant retrovirus derived from a wild type or native retrovirus capable of infecting the cell host concerned. This retrovirus contains parts corresponding to this retrovirus, which are "cis" acting in the wild type virus and which normally are responsible for the packaging of the retrovirus, its reverse transcription into a DNA molecule and its integration into the genome of the cell host, as well as the polyadenylation site of this RNA. This recombinant retrovirus is characterized, in particular, by substituting a deleted part of a hybrid sequence of retrotransposition with a DNA sequence coding for a specific polypeptide under the direct control of a promoter within the hybrid sequence of retrotransposition. Furthermore, the recombinant retrovirus is capable of being recognized by a polymerase of the cell host infected by the above-mentioned native retrovirus. The hybrid sequence of retrotransposition is placed under the control of a promoter outside of this hybrid sequence of retrotransposition (an external promoter) and is included in the genome of the defective retrovirus. Moreover, this defective recombinant retrovirus is characterized by the fact that the relative positions of the coding sequence within the hybrid sequence of retrotransposition and of the external promoter are such that transcription and the expression of the coding sequence under the control of the internal promoter in a host cell infected by the said defective recombinant retrovirus, occurs in a direction opposite to the direction of transcription of the hybrid sequence of transposition under the control of the external promoter.

The defective recombinant retrovirus can be used for the purpose indicated above by infecting this recombinant retrovirus in mammalian cells capable of being infected by the corresponding native retrovirus and, if required, recovering the cells in which the coding sequence is expressed.

Because of its defective character, the recombinant retrovirus according to the present invention cannot replicate in these cells although it preserves its infectious character toward them. It can also be integrated in the form of a provirus into the genome of cell hosts. The coding sequence contained in the hybrid sequence of retrotransposition can then be expressed under the control of the "internal promoter" of the hybrid sequence of retrotransposition.

The internal promoter may consist of any promoter recognized by the polymerases of the infected host, for example, a SV40 or thymidine kinase promoter in the case of cells belonging to cell lines of higher mammals, for example humans or hamsters (for example, CHO cells).

A defective recombinant retrovirus conforming to a preferred embodiment of the invention is characterized in that the distinct external promoter is that of the $LTR^{5'}$ region of the corresponding retrovirus.

More particularly, the genome of a defective recombinant retrovirus of this type comprises successively:

— the $LTR^{5'}$ region of the corresponding wild type retrovirus followed by the packaging region;
— the initiation site of the RNA corresponding to the viral proteins normally encoded by the gag, pol and env genes;
— the hybrid sequence of the retrotransposition in the above-defined orientation replacing all or part of the retroviral region containing these gag, pol and env genes, wherein this hybrid sequence of the retrotransposition is placed under the control of a suitable external promoter included in the genome of the retrovirus, and if appropriate, that of the $LTR^{5'}$ itself; and
— the $LTR^{3'}$ region, which coincides with the polyadenylation site of the corresponding wild type retrovirus.

The invention relates more particularly to the recombinant DNAs (and parts of recombinant DNAs) which permit production of the above-mentioned defective recombinant retroviruses, as well as a procedure for the construction of the above-mentioned recombinant retroviruses.

An example of a recombinant DNA (hereafter designated by the expression "defective recombinant retrovirus DNA") derived from a wild type or native retrovirus and which can be used for the production of the above-mentioned defective recombinant retrovirus is a DNA containing (a) the parts corresponding to those which are "cis" acting in the wild type virus and which are normally responsible for the packaging of this retrovirus, its reverse transcription into a DNA molecule and its integration into the genome of the cell host, and (b) the polyadenylation site of the corresponding RNA. This recombinant retrovirus DNA is more particularly characterized by a deletion of a region corresponding to at least a part if not the totality of the sequences coding for the viral proteins of the wild type or native virus. The part deleted is sufficiently large to prevent the replication of the defective retrovirus capable of being produced in a suitable, competent cell host transformed with this defective recombinant retrovirus DNA. Substitution of this deleted part by a recombinant gene, the structure of which is defined below and which is capable of being transcribed under the control of a distinct external promoter included in the recombinant retrovirus DNA, also characterizes this example.

This recombinant gene is more particularly characterized by the fact that it contains a sequence coding for the desired specific peptide within the recombinant gene, placed downstream from an internal promoter in the direction of transcription imposed by this promoter. In addition, the recombinant gene is characterized by the intercalation between the internal promoter and the coding sequence of a hybrid fragment containing a sequence suitable for blocking transcription. This blocking sequence is flanked at its two opposite extremities within the hybrid fragment by a donor splicing site on the coding sequence side, and by an acceptor splicing site on the side of the promoter. As a consequence, the intercalated elements prevent the transcription of the coding sequence under the control of the internal promoter. Furthermore, when this recombinant gene is placed entirely under the control of an external promoter distinct from the one just mentioned, under conditions such that this recombinant gene can (in the absence of an interrupting codon) be transcribed in sense (reverse direction) to that of the internal promoter, the result is that in a competent cell host the entire recombinant gene is transcribed under the control of the external promoter into messenger RNA from which excises the intercalated region between the internal promoter and the coding sequence (i.e., the region containing the blocking sequence, flanked by the above-mentioned donor and acceptor splicing sites at its two opposite extremities). In the messenger RNA obtained, the RNA sequence corresponding to the sequence coding for the specific polypeptide is thus placed under the direct control of the region corresponding to the internal promoter region.

The recombinant gene is then inserted into the defective recombinant retroviral DNA in a manner such that (a) the orientation of this recombinant gene within the retroviral DNA, and (b) the relative positions of this recombinant gene and the external promoter, are such that the transcription of the recombinant gene under the control of this external promoter can be brought about in cell hosts to insure the production of the defective recombinant retrovirus in an opposite direction to that under which the transcription of the sequence coding for the desired peptide would be brought about, if it were not prevented by the above-mentioned intercalated sequence.

Thus, starting from such a defective recombinant retroviral DNA, it is possible to produce the above-mentioned defective recombinant retrovirus by transfection of an auxiliary cell line (also known as packaging cells or helper cells) which contains in its own genome a nucleic acid sequence (designated hereafter as "complementation sequence") capable of making up for the absence in the defective recombinant vector of sequences coding for the viral proteins necessary for its propagation in the cells of which it is capable of infecting.

This defective recombinant retrovirus is produced by culturing an auxiliary cell line transfected under conditions permitting the replication of this recombinant retrovirus in situ, supplying by complementation the viral proteins encoded in the above-mentioned "trans acting complementation sequence"; and recovering the defective recombinant virus produced in the supernatant of the culture of the auxiliary cell line.

In particular, the complementation sequence contains the part of the genomic DNA of the corresponding wild type, retrovirus coding in particular for the viral proteins of the gag, pol and env genes, which the defective recombinant retrovirus itself lacks.

The transcription of the above-mentioned recombinant gene, under the influence of the external promoter contained in the defective retroviral DNA, subsequent to transfection of a competent cell host under conditions which have been described above, thus produces the corresponding defective recombinant retrovirus in which the sequence coding for the specific polypeptide is placed under the direct control of the internal promoter as set forth above.

The "blocking sequence" contained in the recombinant gene advantageously contains a polyadenylation site. Any other "blocking sequence" can also be used. The "blocking sequence" may contain a sequence containing several initiation and termination codons in the direction of transcription imposed by the internal promoter. It will be obvious from the preceding discussion that the sequences of nucleotides forming the recombinant gene are selected such that the entire recombinant gene may be transcribed starting from an external promoter in the reverse direction.

Advantageously, the recombinant gene is placed under the control of a promoter region corresponding to the LTR$^{5'}$ region of the wild type retrovirus. A preferred defective recombinant retroviral DNA of the present invention consequently consists of the following sequences:

—the LTR$^{5'}$ region of the corresponding wild type retrovirus, followed by the packaging region;

—the initiation site of RNA transcription of the gag, pol and env genes;

—the recombinant gene, defined and in the orientation above, replacing all or part of the retroviral region containing gag, pol and env genes, placed under the control of a suitable external promoter, and if appropriate, that of the LTR$^{5'}$ region itself; and —the LTR$^{3'}$ region, which coincides with the polyadenylation site of the RNA of the corresponding wild type retrovirus.

In one of the preferred embodiments of the invention, the coding sequence, placed under the control of an internal promoter, codes for a protein which is toxic to the cells capable of being infected by the retrovirus. It should be noted that when the defective recombinant retrovirus is produced in auxiliary cell lines, these auxiliary cell lines will be protected against the toxic protein due to the blocking of the transcription of this coding sequence by the intercalated blocking sequence. Cells which can be infected by the native and the present defective recombinant retrovirus can become sensitive, and can even be destroyed, after infection with the defective recombinant retrovirus. The provirus which is thus formed becomes integrated into the genome of the cells and this integration results in the expression of the coding sequence under the control of the internal promoter.

Other coding sequences can naturally be incorporated into the defective recombinant retrovirus. These may be, for example, markers. In this case the invention provides a technique for labelling cells capable of being infected by a retrovirus corresponding to a specific wild type retrovirus, the coding sequence thus behaving as an "indicator" of cell infection.

Another application of the invention is the selective destruction of cancerous cells within a healthy tissue, in particular when the cancerous cells carry an antigen specific for cancerous cells. Such a selective type of destruction becomes possible as soon as an antibody is available which recognizes (a) the specific antigens of these cancerous cells, and (b) the viral proteins of the recombinant retrovirus. When these antibodies bind to the antigens and the viral proteins in question, they are brought in close contact by an intermediary a second class of antibody containing both of the first types of antibody, with the possibility of integrating the defective virus into cancerous cells.

Other characteristics of the invention will also become apparent during the course of the description which follows of assays designed to demonstrate the operational character of defective recombinant retroviruses in conformity with the invention.

The experiments described below were carried out by using a defective provirus derived from murine leukemia Moloney retrovirus, the structure of which is representative of most of the retroviruses capable of infecting the cells of higher mammals. The person skilled in the art will understand that the assays described below can be extended in the same fashion to other types of retroviruses.

A more detailed description of the figures will make it easier to understand the following description of the assays which are presented.

Figure 1:
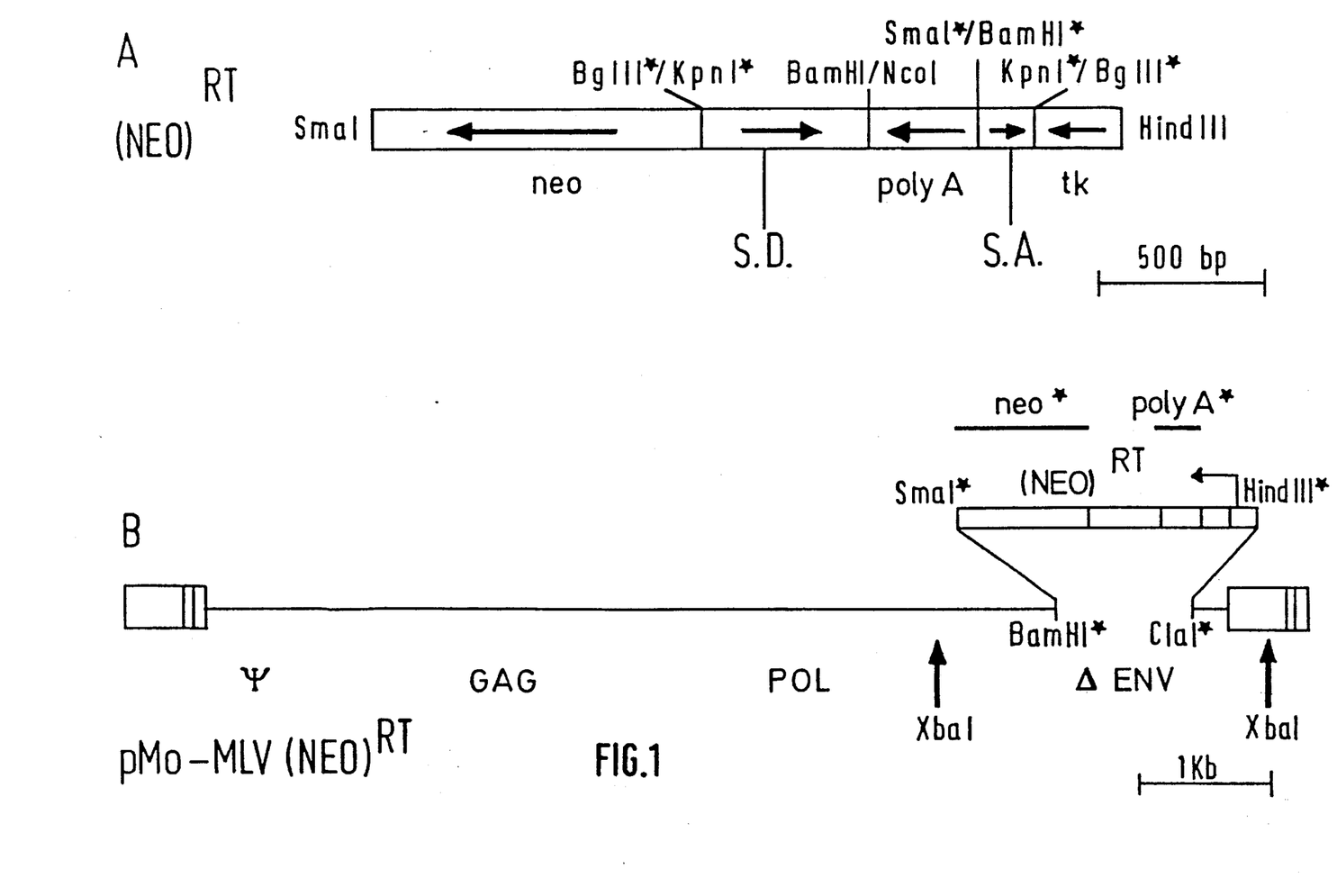
FIGS. 1A and 1B show schematically the construction of a recombinant gene in conformity with the invention, and its insertion into a defective retroviral vector.

FIG. 1 shows the basic elements for the detection of retrotransposition. FIG. 1A shows the structure of $(neo)^{RT}$, an indicator gene for the retrotransposition. This indicator gene corresponds to the "recombinant gene" incorporated in place of one of the regions of the genome of the native retrovirus which codes for its structural proteins (in particular the ENV gene). The orientation of each genetic element is indicated by arrows extending from the corresponding rectangle:

tk represents the promoter of the thymidine kinase gene of HSV;

polyA represents the polyadenylation sequence of the gene previously mentioned;

neo represents the sequence of the gene coding for resistance of neomycin;

D. S. and A. S. represent the donor and acceptor splicing sites, respectively.

In FIG. 1B, the structure of pMo-MLV-$(neo)^{RT}$ of the recombinant retrovirus into which the above-mentioned recombinant gene has been incorporated is illustrated. The retroviral part of the construction is derived from the cloned provirus pMov3. FIG. 1 is also shows the neo fragments (the "indicator" fragment of the recombinant retrovirus in which the above-mentioned recombinant gene has been incorporated) and the polyA (the blocking sequence).

In FIGS. 1A and 1B the restriction sites used for the construction of the plasmids are marked with an asterisk when they are eliminated.

Figure 2:
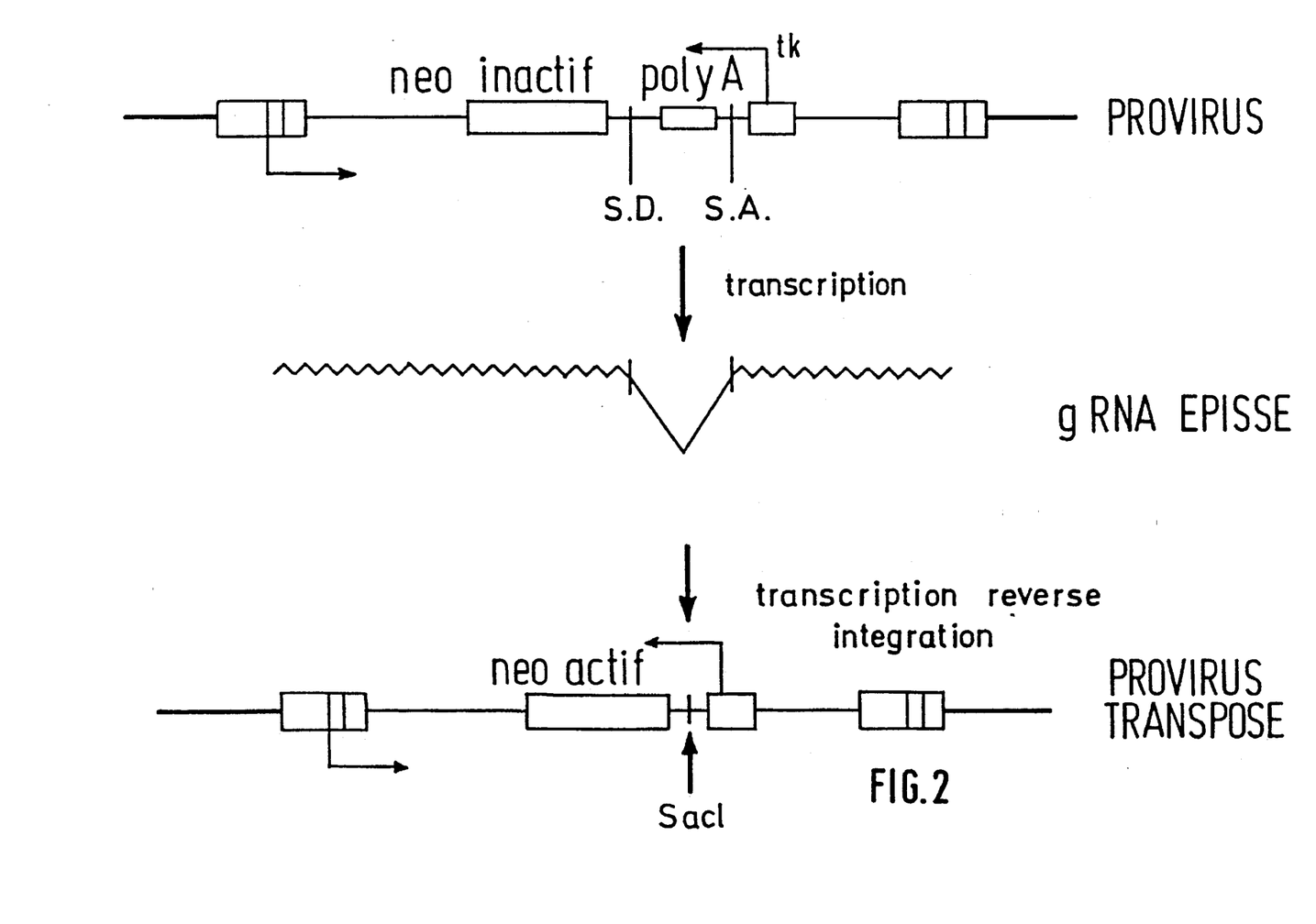
FIG. 2 shows a schematic representation of the successive steps of integration of a defective recombinant retrovirus in the form of a provirus, starting from the recombinant DNA of FIG. 1, into an infected cell and the steps of its transcription into messenger RNA and its reverse transcription, followed by integration into the genome of the infected cell.

FIG. 2 shows the successive stages of the production of the defective retrovirus according to the invention, involving the intermediate formation of RNA (spliced gRNA) by transcription of the recombinant retroviral DNA, which leads to the provirus, which is integrated into the genome of an infected cell by the defective recombinant retrovirus.

FIG. 3 (Panels A and B) illustrates a "Southern blot" analysis of the DNA of the genome of the G418-resistant cells infected with the virus obtained from cells transfected with pMo-MLV$(neo)^{RT}$.

The cells derived from the clone 3T3gptMo$(neo)^{RT}$-A (a 3T3 clone obtained by transfection with pSV2gpt and pMo-MLV$(neo)^{RT}$) were infected with the Mo-MLV viruses. The supernatant was collected after seven days and 100 µl of this supernatant was used to infect $10^4$ 3T3 test cells. Two days later these cells were subjected to selection in the presence of G418. The G418-resistant cells were analyzed either in the form of a population of mixed clones (3T3 Mo$(neo)^{RT}$ population), or in the form of individual clones (3T3 Mo$(neo)^{RT}$ c11 to c17).

The restriction enzymes used to verify that splicing had been carried out correctly XbaI (X) and XbaI+SacI (X+S). 10 or 25 µg of DNA was used (the two first bands). The filters were hybridized with either the neo probe (BglII-SmaI fragment, FIG. 3A) or the polyA probe (SmaI-NcoI fragment, FIG. 3B).

FIG. 4 (Panels A and B) illustrates a Southern blot analysis of the DNA of the genomes of cells resistant to G418 isolated from clones transfected with 3T3gptMo$(neo)^{RT}$ and the sequence of a splicing junction.

Figure 3A:
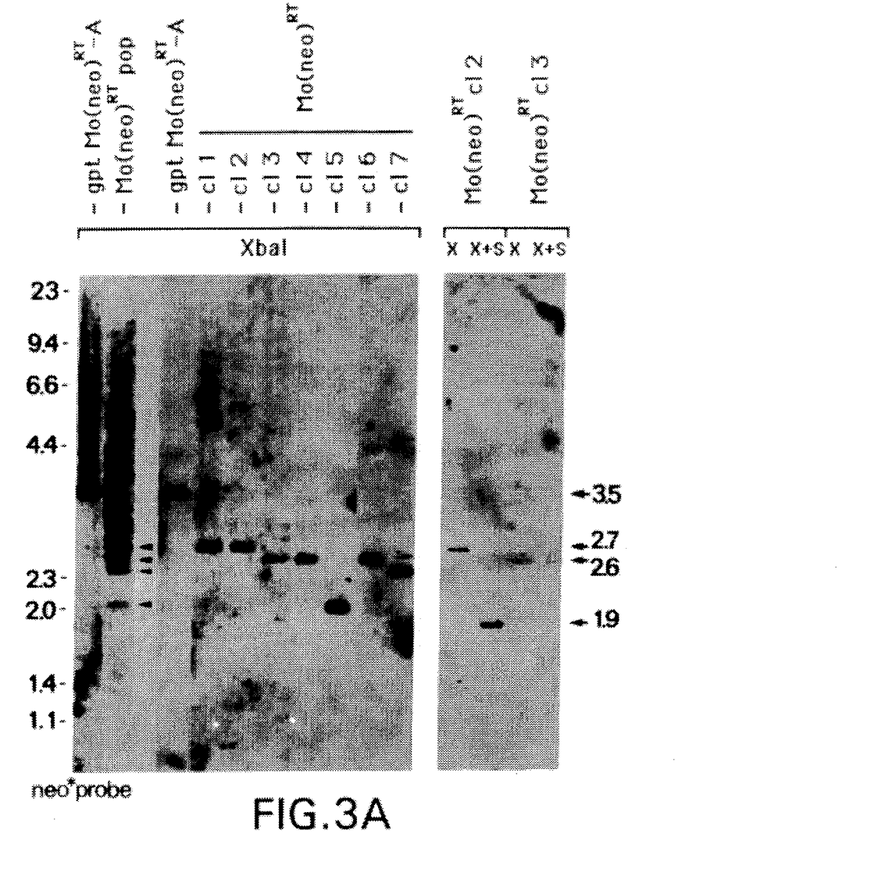
FIGS. 3 and 4 are schematic representations of the fractionation on a gel of the different fragments of DNAs tested, after digestion by various restriction enzymes of the DNAs extracted from the infected cells.
Figure 3B:
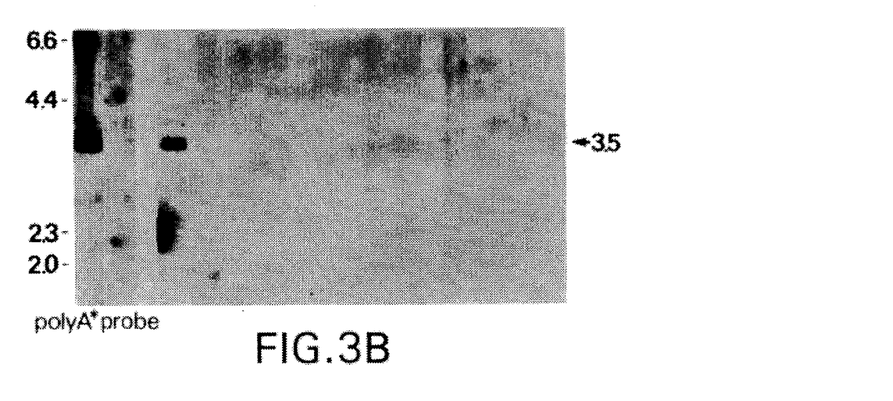
Figure 4A:
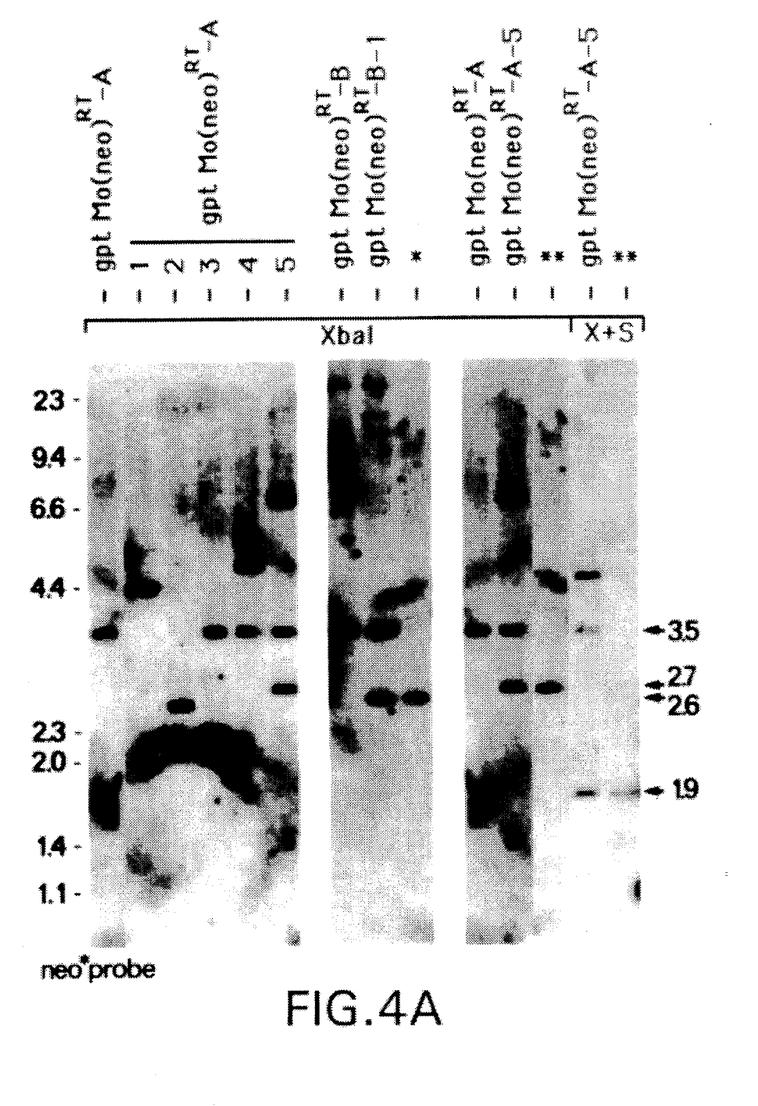
Figure 4B:
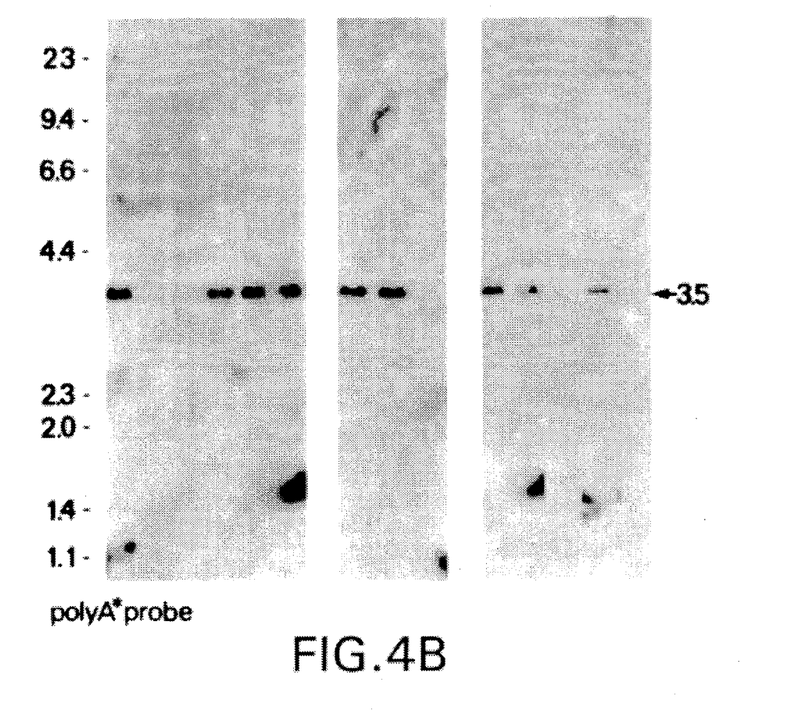

In the procedures used to produce the blots of FIGS. 4A and 4B, $10^7$ cells derived from the clones 3T3gptMo$(neo)^{RT}$ were subjected to selection in the presence of G418 ($10^6$ cells/10 cm of plaque). 0–2 clones resistant to G418 per plaque were obtained (see, for example 3T3gptMo$(neo)^{RT}$ clones A-1 to A-5 and clone c11 B-1). The DNA was analyzed as described in FIG. 2, after restriction with XbaI and XbaI+SacI to confirm that splicing had been done correctly. The new copies in the B-1 and A-5 clones co-migrate with the 2.6 kb and 2.7 kb XbaI fragments of the clones Mo$(neo)^{RT}$ C13 (,) and c12 (**), respectively, of FIG. 3. The filters were hybridized with the neo probe FIG. 4A or the polyA probe FIG. 4B.

Figure 4C:
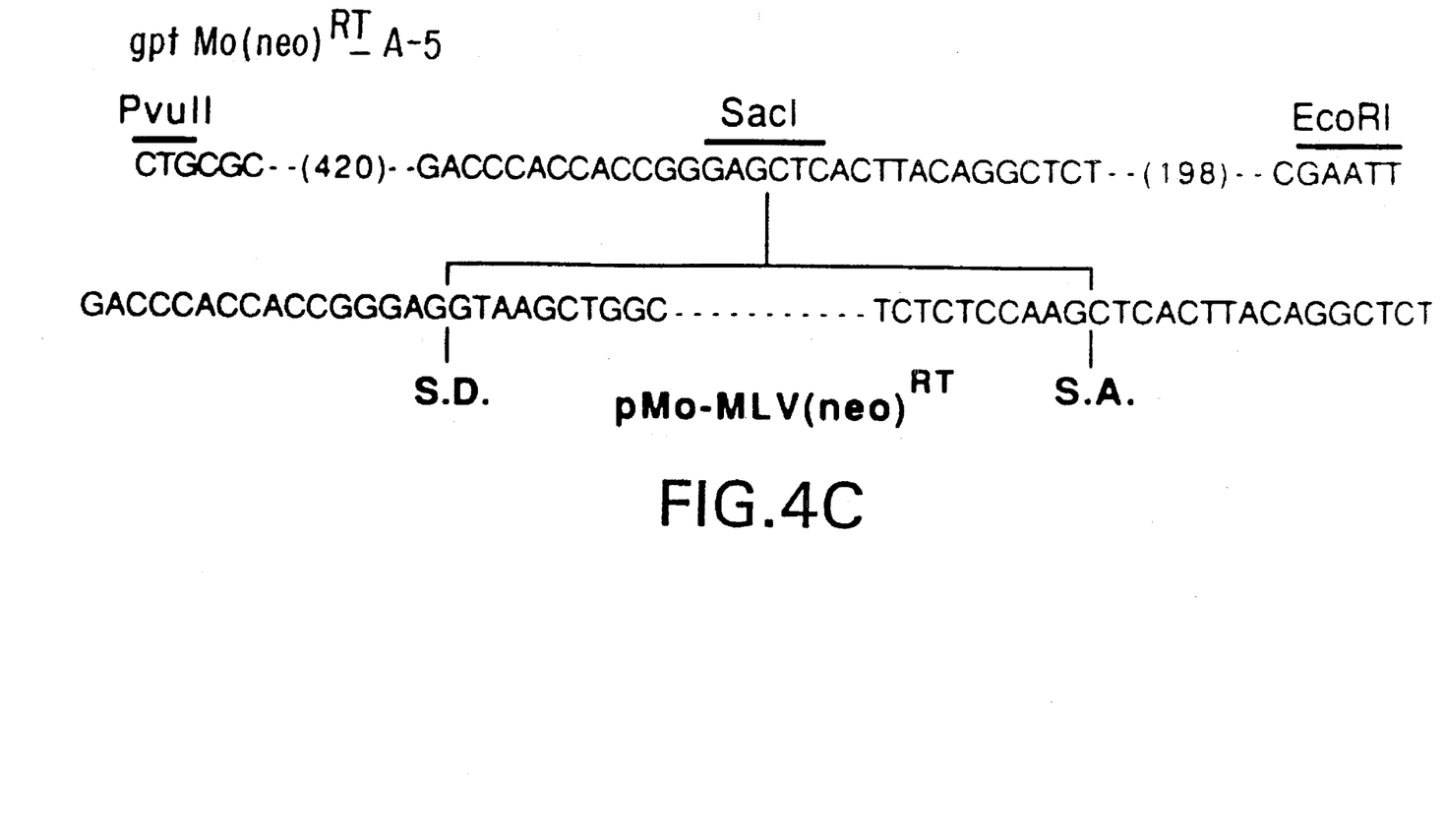

FIG. 4C shows the sequence of a splicing junction in a transposed proviral copy of pMo-MLV$(neo)^{RT}$.

The 2.7 kb XbaI fragment derived from the DNA of 3T3gptMo$(neo)^{RT}$-A-5 was cloned into λgt10, and a fragment of 662 based pairs defined by the PvuII site situated in the coding neo region and by the EcoRI site situated in the promoter tk, was subcloned into M13 and sequenced. The new SacI site which appeared at the splicing junction is indicated.

1) Materials and Methods a) Construction of the plasmids

In order to construct the indicator of retrotransposition $(neo)^{RT}$, the sequence coding for the polyadenylation of the thymidine kinase gene of Herpes Simplex virus was isolated from the plasmid pAGO (COLBERE-GARAPIN, F. et al., *J. Mol. Biol.*, 150, 1–14 (1981)) in the form of a SmaI-NcoI fragment having 310 base pairs, and was inserted at the unique BamHI site of the plasmid pZip (CEPKO, C. L., et al., *Cell.* 37, 1053–1062 (1984)), between the Moloney donor and acceptor splicing sites, after treatment of the two fragments with the Klenow enzyme. The fragment containing the polyadenylation sequence and the splicing sites was then isolated from a KpnI-KpnI fragment, and inserted between the promoter SVtk and the region coding for the gene (neo) at the BglII site of pSVtk-neobeta (NICOLAS, J. S. and BERG, P., in *Cold Spring Harbor Conferences on Cell Proliferation*, Silver, L. M., MARTIN, G. R. & Strickland, S. S., eds., 10, 469–485 (1983)). After treatment of the two fragments with the Klenow enzyme, the indicator gene $neo^{RT}$ (FIG. 1A) was isolated from a HindIII-SmaI fragment.

In order to suppress the env genes in the plasmid pMov3 (HARBERS, K., et al., *Proc. Natl. Acad. Sci.*, USA, 78, 7609–7613 (1981)), the EcoRI fragment of the pMVO3 plasmid was first recloned in the 3.4 kb EcoRI fragment of pSVtk-neobeta. The BamHI-ClaI fragment (corresponding respectively to the base pairs 6537 and 7674 described in *RNA Tumor Viruses*, WEISS, R., TEICH, N., VARMUS, H. & COFFIN, J., eds. 2, 766–767 (1985)) coding for a part of the gp70 protein and for the whole of the p15E protein was then removed by complete digestion with the aid of ClaI and by partial digestion with BamHI.

The final construction (pMo-MLV$(neo)^{RT}$) was obtained by ligation of the pMov3 vector, the env genes of which were suppressed in the manner indicated above, with the indicator gene $(neo)^{RT}$ after treatment with the Klenow enzyme (FIG. 1B).

b) Culture of cells, transfection and infection

These methods are described in JACOB, H. and NICOLAS, J. S., *Methods in Enzymol.*, 151, 66–81 (1987). The cells used were NIH 3T3 and FG10 (FINSHINGER et al.,

*Virology*, 59, 217–229 (1974)), and the viral lines used were 3T3 Mo-MLV for Moloney and E40psiB for Mo-MLVneo (RUBENSTEIN, J. L. R. et al.; *Proc. Natl. Acad. Sci.*, USA, 81, 7137–7140 (1984)). The selection of the G418-resistant cells was carried out in the presence of 600 µg/ml of geneticin (G418), and the cells containing pSV2gpt (MULLIGAN, R. C. et al., *Pro. Natl. Acad. Sci.*, USA, 78, 2072–2076 (1981)) were selected in the presence of 25 µg/ml of mycophenolic acid and 250 µg/ml of Xanthine.

The infections were carried out as described in JACOB, H. and NICOLAS, J. F. (1987) supra in the presence of 5 µg/ml of polybrene.

c) Analysis of the DNA of the cells

For the Southern blot analysis, the genomic DNA treated with suitable restriction enzymes was subjected to electrophoresis, transferred to HYBOND-N nylon membranes (AMERSHAM), and hybridized to probes radioactively labelled with $p^{32}$ (MULTIPRIME kit sold by AMERSHAM).

d) Cloning and sequencing of the splicing junction site

50 µg of the DNA derived from the 3T3 gPtMo(neo)$^{RT}$-A-5 clone was digested with XbaI and subjected to electrophoresis in a 0.7% agarose gel. An agarose band comprising fragments of from 2.5 to 2.9 kb was cut out, and the DNA extracted by electroelution was used to construct a partial gene bank in the vector λgt 10, according to standard procedures and using EcoRI linkers (HUYNH et al., *DNA Cloning*, Glover, D. M., ed., IRL Press, N.Y. 1, 49–78 (1985)). The clones were selected by hybridization with the neo probe labelled with $p^{32}$ on a membrane filter. PvuII-EcoRI fragments derived from positive clones were subcloned into the vector M13mp10 and sequenced by the method described in SANGER, F. et al. (*Proc. Natl. Acad. Sci.*, USA, 74, 5463–5467 (1977)).

2) Results a) Principle of the assay

The principle of the assay is based on the use of a gene selection which can be activated by an RNA-mediated transposition (FIG. 1). A gene (tkneo) is inactivated by insertion of a signal and a site for polyadenylation (polyA) between the promoter (tk) and the structural part of the gene. The sequence for polyadenylation on the non-coding DNA strand is surrounded by the donor and acceptor splicing sites (neo$^{RT}$, FIG. 1A). When the polyA sequence is inserted in a reverse orientation in a retro-transposon (pMo-MLV(neo)$^{RT}$, FIG. 1B), the reverse transcription of the non-coding spliced neo$^{RT}$ RNA leads to the formation of a DNA structure in which the neo gene is placed under the control of the promoter tk. A cell containing a retrotransposed copy consequently becomes resistant to G418.

In the neo$^{RT}$ gene, (1) the expression of the selected gene is expected to be maintained as long as the polyA region is present in the intron sequence and (2) the suppression of the polyA region creates a structure conferring resistance to G418 on cell hosts.

These two last points, and the non-viral retrotransposition of the retroviruses, were assayed by insertion of the neo$^{RT}$ gene in a cloned Mo-MLV provirus. The genes of the provirus which code for the major components of the viral envelope were suppressed.

b) pMo-MLV(neo)$^{RT}$ does not confer resistance to G418

In order to prove that (neo)$^{RT}$ satisfies the two points previously mentioned, it was introduced into NIH 3T3 cells by transfection of pMo-MLV(neo)$^{RT}$. pSV2gpt was co-transfected, thus leading to the isolation of clones in which pMo-MLV(neo)$^{RT}$ is not introduced selectively (3T3 gpt-Mo(neo)$^{RT}$ clones), and thus enabling one to measure the efficacies of transfection.

In a first inactivation assay of the neo gene in neo$^{RT}$, the population of transfected cells was directly subjected to selection in a medium containing the antibiotic G418, and the number of resistant clones was compared with those obtained by transfection of a plasmid in which the neo gene is active (pMo-MLVneo, RUBENSTEIN, J. L. R. et al. (1984) supra). pMo-MLV(neo)$^{RT}$ leads only to the production of 0–3 clones resistant to G418 per transfection (3 experiments), whereas more than 75 clones resistant to G418 were obtained with the plasmid pMo-MLVneo. A parallel selection in a medium containing mycophenolic acid shows that the efficacies of transfection are identical (Table 1).

A Southern analysis of the structure of 5 individual clones resistant to G418 indicated the presence of rearrangements (probably due to transfection) of a 3.5 kb XbaI fragment which contains the indicator gene (shown in FIG. 1A).

In a second assay, the clones were selected on the basis of the expression of gpt, and 7 of them containing a non-rearranged (neo)$^{RT}$ gene (see, for example, the clones 3T3gptMo(neo)$^{RT}$-A and B of FIG. 3) were subjected to G418. None of them was resistant to G418 (see also the following paragraphs).

These experiments show that the (neo)$^{RT}$ gene does not confer resistance to G418, unless it is rearranged.

c) Sequence resulting from the reverse transcription of pMo-MLV(neo)$^{RT}$ confers resistance to G418

A fraction of the RNA produced by pMo-MLV(neo)$^{RT}$ in the transfected cells must be spliced. Consequently, it does not contain a polyadenylation sequence. This RNA conserves the properties of an RNA of the viral genome which, as a result of a transcomplementation mechanism of viral products, must be packaged within viral particles. In order to test whether the copies obtained by reverse transcription (FIG. 1C) can confer resistance to G418, the supernatants of 3T3gptMo-(neo)$^{RT}$ cells infected with the Mo-MLV virus were transferred to NIH 3T3 test cells.

Colonies resistant to G418 were obtained starting from supernatants of 7 transfected 3T3gpt(neo)$^{RT}$ clones mentioned above. The titer of the supernatants varied from 0.5 to $2\times10^3$ neo$^{RT}$pfu/ml. The structure of the new proviruses was analyzed by Southern blot.

As described in FIG. 2A, the XbaI fragment containing (neo)$^{RT}$ observed in the 3T3gptMo(neo)$^{RT}$ clones with the neo probe is smaller in the population of infected cells (population Mo(neo)$^{RT}$) or in the sub-clones (Mo(neo)$^{RT}$c11 to c17). It is possible to observe up to four bands of unequal intensities in the population, two of which (2.7 and 2.6 kb) are the major bands represented in the sub-clones. Of 25 clones infected and analyzed, 8 contained the 2.7 kb band and 12 the 2.6 kb band. The two other bands observed were smaller (2.5 kb and 2.0 kb), and the original 3.5 kb band was never observed. None of these four bands hybridized with the polyA probe of the intron region (FIG. 2B).

The 2.7 kb band was studied in more detail in order to determine whether it contained the SacI site which would be expected to appear at the splicing junction (MANN, R. et al., *J. Virol.*, 54, 401–407 (1985); FIG. 1C). The 2.7 kb fragment is in fact reduced to a 1.9 kb fragment when the genomic DNA is digested with the restriction enzymes XbaI and SacI and subjected to a hybridization test using the neo probe. In contrast, the 2.6 kb band did not contain the SacI site, and must be linked to splicing events involving cryptic sites D-A or to rearrangements during reverse transcription.

In conclusion, pMo-MLV(neo)$^{RT}$ can give rise, via an RNA intermediate, to structures in which the neo gene is active.

d) Retrotransposition of the Moloney env provirus $10^8$ cells derived from four independent 3T3gpt(neo)$^{RT}$ clones were subjected to G418 selection. In each case, 1 to 10 resistant clones per $10^7$ cells were obtained, and their DNA was analyzed (FIG. 3). They can be classified in two groups.

In the first group (13 out of 37 clones resistant to G418), the 3.5 kb XbaI fragment (corresponding to the transfected plasmid of FIG. 1A) was replaced by a new fragment (FIG. 3, c11 and c12), which does not hybridize with the polyA intron probe (FIG. 3B). These clones may thus be rearrangements of the initial copies in which at least the polyA sequence is suppressed.

In the second group (24 out of the 37 clones analyzed), one and sometimes two bands hybridizing with the neo probe are observed in addition to the initial 3.5 Kb band of the transfected clones (FIG. 3A, clones A-3 to A-5 and B-1). These additional bands do not hybridize with the polyA probe (FIG. 3B). In several cases (5 and 2 clones, respectively), these bands co-migrate either With the 2.6 kb splicing copy, or with the 2.6 kb copy of the infected clones (FIG. 3A, clones A-5 and B-1). The fact that the 2.7 kb band was derived from the reverse transcription of a correctly spliced transcription sequence of the transfected provirus was demonstrated by digestion of the DNA with XbaI and SacI which generates a band of 1.9 kb (FIG. 3A, clone A-5). This conclusion was confirmed by cloning a 2.7 kb XbaI fragment starting from one of the G418 clones resistant at 64.8 (clone A-5) and by sequencing the splicing junction site (FIG. 3C).

Thus, it follows from the preceding assays that a recombinant RNA can be obtained which, after reverse retranscription, produces a recombinant DNA capable of giving rise to messenger RNA containing an RNA sequence corresponding to the neo sequence. In turn, the RNA sequence corresponding to neo can be translated under the control of the internal promoter which is linked to it, starting from the neo$^{RT}$ gene in the defective retrovirus (behaving as a retrotransposon) in an orientation such that the splicing sites are contained in a nucleic acid sequence transcribed starting from an external promoter of the retrovirus in a direction opposite to the normal direction of transcription of the neo marker, under the control of the internal promoter of neo$^{RT}$.

It should be noted that the transcomplementing lines in which the defective recombinant retrovirus of the invention can be produced are available from the American Type Culture Collection (ATCC) under the designation ψ2.

We claim:

1. A defective recombinant retroviral DNA comprising a 5' LTR, a recombinant gene, a 5' splice donor site, a polyadenylation sequence, a 3' splice acceptor site, an internal promoter, and a 3' LTR, wherein:

said recombinant gene consists of a nucleic acid sequence encoding a polypeptide toxic to a competent eukaryotic cell host;

said internal promoter is recognized by a DNA polymerase present in said competent eukaryotic cell host and said internal promoter controls transcription of said recombinant gene;

said internal promoter and recombinant gene are present in said recombinant retroviral DNA in an orientation opposite to the direction of transcription from said 5' LTR;

said polyadenylation sequence is inserted in the same orientation as, and between, said internal promoter and said recombinant gene, said polyadenylation sequence blocking transcription of said recombinant gene from said internal promoter;

said polyadenylation sequence is flanked on one side by a 5' splice donor site and flanked on the other side by a 3' splice acceptor site, said 5' splice donor site and 3' splice acceptor site being located on the DNA strand antisense to said recombinant gene, polyadenylation sequence and promoter; and said 5' splice donor site and 3' splice acceptor site are transcribed from the 5' LTR.

2. The defective recombinant retroviral DNA of claim 1, wherein said recombinant gene, 5' splice donor site, polyadenylation sequence, 3' splice acceptor site, and internal promoter replace all of the gag, pol and env genes of the wild type retrovirus from which the defective recombinant retroviral DNA is derived.

3. The defective recombinant retroviral DNA of claim 1, further comprising the retroviral packaging region and the initiation site of RNA transcription of the gag, pol and env genes of the wild-type retrovirus from which the defective recombinant retroviral DNA is derived.

4. The defective recombinant retroviral DNA as in any one of claims 1–3, wherein said competent eukaryotic cell host is a mammalian cell host.

5. A method for producing a defective recombinant retrovirus, comprising the steps of:

transfecting an auxiliary cell line with the defective recombinant retroviral DNA of claim 1;

culturing said transfected auxiliary cell line; and recovering said defective recombinant retrovirus from the supernatant of said auxiliary cell line culture.

6. A method for producing a defective recombinant retrovirus, comprising the steps of:

transfecting an auxiliary cell line with the defective recombinant retroviral DNA of claim 2;

culturing said transfected auxiliary cell line; and recovering said defective recombinant retrovirus from the supernatant of said auxiliary cell line culture.

7. A method for producing a defective recombinant retrovirus, comprising the steps of:

transfecting an auxiliary cell line with the defective recombinant retroviral DNA of claim 3;

culturing said transfected auxiliary cell line; and recovering said defective recombinant retrovirus from the supernatant of said auxiliary cell line culture.

8. The method as in any one of claims 5–7, wherein said auxiliary cell line contains DNA encoding the retroviral packaging proteins not encoded by the defective recombinant retroviral DNA.

9. The method according to claim 8, wherein said DNA encoding the retroviral packaging proteins comprises the gag, pol and env genes of the wild-type retrovirus from which the defective recombinant retroviral DNA is derived.

10. A method for incorporating a sequence of nucleotides encoding a toxic polypeptide into the genome of cells in culture, said method comprising introducing into said cells in culture the defective recombinant retroviral DNA of any one of claims 1–3.

11. A defective recombinant retroviral DNA comprising a 5' LTR, a recombinant gene, a 5' splice donor site, a polyadenylation sequence, a 3' splice acceptor site, an internal promoter, and a 3' LTR, wherein:

said recombinant gene consists of a nucleic acid sequence encoding a selectable marker in a competent eukaryotic cell host;

said internal promoter is recognized by a DNA polymerase present in said competent eukaryotic cell host and said internal promoter controls transcription of said recombinant gene;

said internal promoter and recombinant gene are present in said recombinant retroviral DNA in an orientation opposite to the direction of transcription from said 5' LTR;

said polyadenylation sequence is inserted in the same orientation as, and between, said internal promoter and said recombinant gene, said polyadenylation sequence blocking transcription of said recombinant gene from said internal promoter;

said polyadenylation sequence is flanked on one side by a 5' splice donor site and flanked on the other side by a 3' splice acceptor site, said 5' splice donor site and 3' splice acceptor site being located on the DNA strand antisense to said recombinant gene, polyadenylation sequence and promoter; and said 5' splice donor site and 3' splice acceptor site are transcribed from the 5' LTR.

12. The defective recombinant retroviral DNA of claim 11, wherein said nucleic acid sequence encoding a selectable marker is the neo gene.

* * * * *